(12) United States Patent
Ohyagi (10) Patent No.: US 6,422,700 B2
(45) Date of Patent: Jul. 23, 2002

(54) VISUAL ACUITY CHART DISPLAYING APPARATUS

(75) Inventor: Wataru Ohyagi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 09/822,236

(22) Filed: Apr. 2, 2001

(30) Foreign Application Priority Data

Mar. 31, 2000 (JP) ........................................ 2000-097119

(51) Int. Cl.$^7$ ................................................ A61B 3/02

(52) U.S. Cl. ...................................................... 351/239

(58) Field of Search ................................ 351/237, 238, 351/239, 242, 243, 245, 222, 234, 235

(56) References Cited

U.S. PATENT DOCUMENTS 5,883,693 A * 3/1999 Iki .............................. 351/239
5,929,972 A * 7/1999 Hutchinson ................. 351/237

* cited by examiner

*Primary Examiner*—George Manuel
(74) *Attorney, Agent, or Firm*—Armstrong, Westerman & Hattori, LLP (57) ABSTRACT

A visual acuity chart displaying apparatus for displaying various visual charts for a visual performance examination, for an eye to be examined includes, a visual chart plate (4) in which a plural kinds of visual charts displayed for the eye to be examined are arranged changeably, a first mask plate (21) which is disposed in the front of the visual chart plate (4) with an overlapping state and in which a plurality of non-mask portions for performing each single longitudinal row transmission of the visual charts displayed on the visual chart plate (4) are arranged changeably, and a second mask plate (22) which is disposed in the front of the first mask plate (21) with an overlapping state and in which a plurality of non-mask portions for performing each single transverse column transmission of the visual charts displayed on the visual chart plate (4) are arranged changeably. In the visual acuity chart displaying apparatus, visual charts with a predetermined light transmission state formed by one selected from the group including a transverse direction, a longitudinal direction and a combination of these directions, can be displayed for the eye to be examined, outside a predetermined region of predetermined visual charts, by a visual chart changing by the visual chart plate (4) and a mask changing by the first and second mask plates (21, 22).

4 Claims, 8 Drawing Sheets

FIG. 11

VISUAL ACUITY CHART DISPLAYING APPARATUS

BACKGROUND OF THE INVENTION

1. Field of the Invention

The present invention relates to a visual acuity chart displaying apparatus, and in particular, to a visual acuity chart displaying apparatus which is constructed with a space saving type, using, for example, a concave mirror and a half mirror, and used in a visual performance examination with the state that an eye to be examined is made to view a visual chart image.

2. Description of the Related Art

In the case of a conventional eye examination apparatus constructed with a space saving type using a concave mirror and a half mirror, a manner in which the eye to be examined is made to view a predetermined visual chart image is, for example, as follows.

That is, a visual chart plate in which a large number of visual charts are displayed is disposed on an optical path of a visual chart projecting optical system, and one circular mask plate having a plurality of non-mask portions is disposed rotatably, adjacent to this visual chart plate. Then, by a selection and a combination of a predetermined visual chart of the visual chart plate and a predetermined non-mask portion of the circular mask plate, a visual chart with a predetermined transmission state formed by overlapping the predetermined visual chart with the non-mask portion is to be located on the optical path of the visual chart projecting optical system.

Also, as other example that the eye to be examined is made to view a predetermined visual chart image transmitted by masking, a structure has been known such that two circular mask plates having a plurality of non-mask portions are disposed rotatably in succession, adjacent to the visual chart plate, and then, by a combination of each of the non-mask portions of the two circular mask plates, a visual chart with a predetermined transmission state formed by overlapping the predetermined visual chart with the non-mask portion is to be located on the optical path of the visual chart projecting optical system.

However, in the case of the structure using one circular mask plate in the above conventional eye examination apparatus with a space saving type, since the diameter of the circular mask plate, determined from a relationship between the size of this structure and that of the eye examination apparatus itself is limited in size, the number of non-mask portions to be provided is limited, so that the number of visual chart images with various transmission states to be viewed for the eye to be examined is limited. Thus, there is a problem in that an eye performance examination cannot be performed minutely to be sure. On the contrary, when the number of non-mask portions is increased, since the diameter of the circular mask plate becomes larger, the significance of constructing the eye examination apparatus with a space saving type is reduced.

Also, in this structure, when a visual chart with one transmission state is changed into a visual chart with other transmission state by rotating one circular mask plate, since it is the structure using one circular mask plate, a plural kinds of visual chart images appear to flow with respect to a person to be examined which views a visual chart image as if it flows, so that an uncomfortable feeling is generated in the eye to be examined.

Also, in the case of the structure using merely two circular mask plates, merely a plural kinds of non-mask portions are provided at random in each of two circular mask plates, and a sense performance of a third dimension with respect to the eye to be examined which views a visual chart image with a transmission state is not considered at all. As a result, when two circular mask plates are used, a visual chart with a third dimension, that is, with uncomfortable feeling, is viewed for the eye to be examined. Thus, in this case also, there is a problem in that an eye performance examination cannot be performed minutely to be sure.

SUMMARY OF THE INVENTION

The present invention has been made in view of the above problems of the conventional arts, and an object of the present invention is to provide a visual acuity chart displaying apparatus which can be constructed with a space saving type, in which a visual chart image with a predetermined mask state can be viewed smooth and fast without providing the eye to be examined with an uncomfortable feeling, and in which an eye performance examination can be performed minutely to be sure.

According to a first aspect of the present invention, there is provided a visual acuity chart displaying apparatus for displaying various visual charts for a visual performance examination for an eye to be examined, comprising: a visual chart plate in which a plural kinds of visual charts displayed for the eye to be examined are arranged changeably; a first mask plate which is disposed in a front of the visual chart plate with an overlapping state and in which a plurality of non-mask portions for performing each single longitudinal row transmission of the visual charts displayed on the visual chart plate are arranged changeably; and a second mask plate which is disposed in a front of the first mask plate with an overlapping state and in which a plurality of non-mask portions for performing each single transverse column transmission of the visual charts displayed on the visual chart plate are arranged changeably, characterized in that the visual charts with a transmission state can be displayed for the eye to be examined by a combination of a visual chart changing by the visual chart plate and a transmission changing by the first and second mask plates.

According to the first aspect of present invention, since the first mask plate for each single longitudinal row transmission of the visual charts and the second mask plate for each single transverse column transmission are disposed to overlap with each other and then a predetermined transmission is performed outside a predetermined region of the visual charts by a combination of changing in each of the non-mask portions of the first and second mask plates, mask changing with respect to the visual charts can be performed fast and smooth. As a result, the occurrence of the state that the visual chart images viewed by the eye to be examined appear to flow is prevented, and a visual performance examination can be performed without providing the eye to be examined with an uncomfortable feeling.

According to a second aspect of the present invention, there is provided a visual acuity chart displaying apparatus for displaying various visual charts for a visual performance examination, for an eye of a person to be examined, characterized by comprising: a visual chart plate in which a plural kinds of visual charts displayed for the eye to be examined are arranged changeably in a circle; a display optical system for displaying the visual charts of the visual chart plate at a predetermined distance from the eye to be examined; an illumination optical system including a light source for illuminating the visual charts; a mask mechanism including, a first mask plate with a disk shape, which is disposed in a front of the visual chart plate with an overlapping state and in which a plurality of first non-mask portions for performing each single longitudinal row transmission of the visual charts displayed on the visual chart plate are arranged changeably, and a second mask plate with a disk shape, which is disposed in a front of the first mask plate with an overlapping state and in which a plurality of second non-mask portions for performing each single transverse column transmission of the visual charts displayed on the visual chart plate are arranged changeably; indication means for indicating a predetermined transmission state by predetermined visual charts and the plurality of first and second non-mask portions; and a drive system for driving the visual chart plate, the first mask plate and the second mask plate individually to rotate in accordance with indication information by the indication means, so that visual charts with the predetermined transmission state formed by one selected from the group including a transverse direction, a longitudinal direction and a combination of these directions, are displayed outside a predetermined region of the predetermined visual charts.

According to the second aspect of the present invention, when the predetermined transmission state by the predetermined visual charts and the plurality of first and second non-mask portions of the first and second mask plates is indicated by the indication means, the drive system drives the visual chart plate, the first mask plate and the second mask plate individually, so that the visual charts with the predetermined transmission (for example, one character transmission) state formed by one selected from the group including a single transverse column, a single longitudinal row and a combination of these, are located on a visual chart projecting optical system.

Therefore, the predetermined visual chart images with the predetermined transmission state can be displayed for the eye to be examined, the occurrence of the state that visual chart images viewed by the eye to be examined appear to flow Is prevented as in the first aspect of the present invention, and a visual performance examination can be performed without providing the eye to be examined with uncomfortable feeling. Also, since it is constructed by using the first and second mask plates, in comparison with the case where a single mask plate is used, the diameter of each of the mask plates can be made small, and thus a further space saving type can be obtained.

DETAILED DESCRIPTION OF THE PREFERRED EMBODIMENT

An embodiment of the present invention will be described below in detail.

Figure 1:
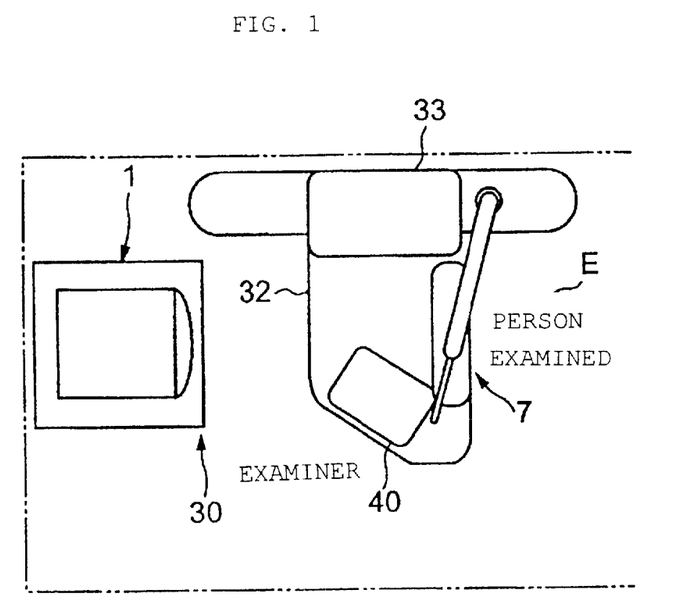
FIG. 1 is a schematic plan view representing the entire structure of an eye examination system according to an embodiment of the present invention.
Figure 2:
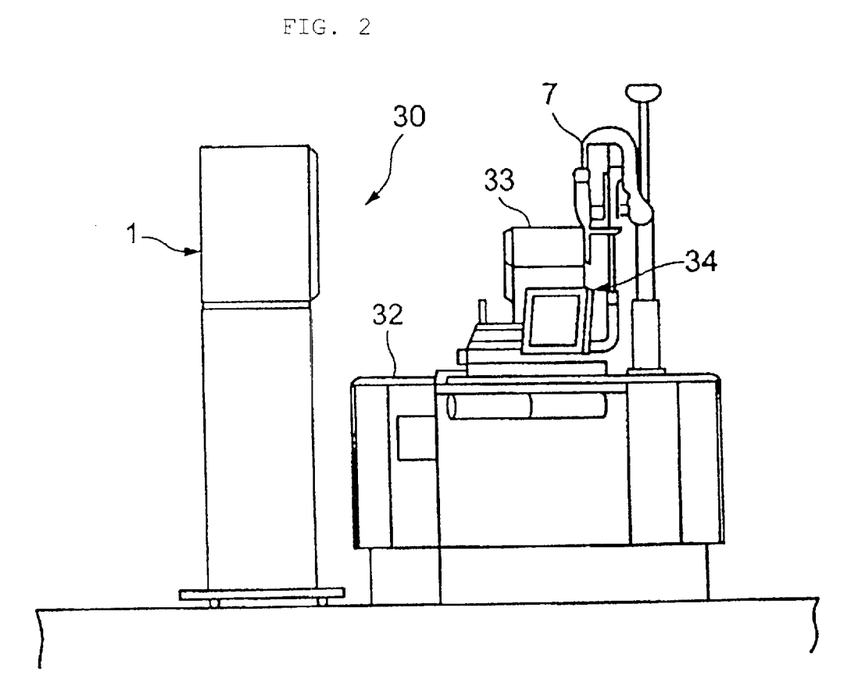
FIG. 2 is a schematic side view representing the entire structure of the eye examination system according to the embodiment of the present invention.

FIGS. 1 and 2 show the entire structure of a so-called space saving type eye examination system including an eye examination unit 7 and a visual chart displaying means 1, according to the embodiment of the present invention.

This eye examination system includes, the eye examination unit 7 and a reflect meter 33, which are disposed on an eye examination table 32, the box shaped visual chart displaying means 1 as a visual acuity chart displaying apparatus, an operation displaying unit 34, and a remote controller 55 as instructing means. The visual chart displaying means 1 is disposed opposite to the eye examination unit 7 as eye examination means to be disposed, (which is apart from by, for example, a distance L), in the position apart from the eye examination table 32 by a predetermined distance L. The operation displaying unit 34 is disposed on the eye examination table 32 and performs various operation inputs and a display of eye examination information. The remote controller 55 is disposed on the eye examination table 32 or in an arbitrary position and instructs such that a predetermined visual chart becomes in a predetermined mask state, by performing communication (for example, infrared data communication) with the visual chart displaying means 1 by wireless.

Figure 3:
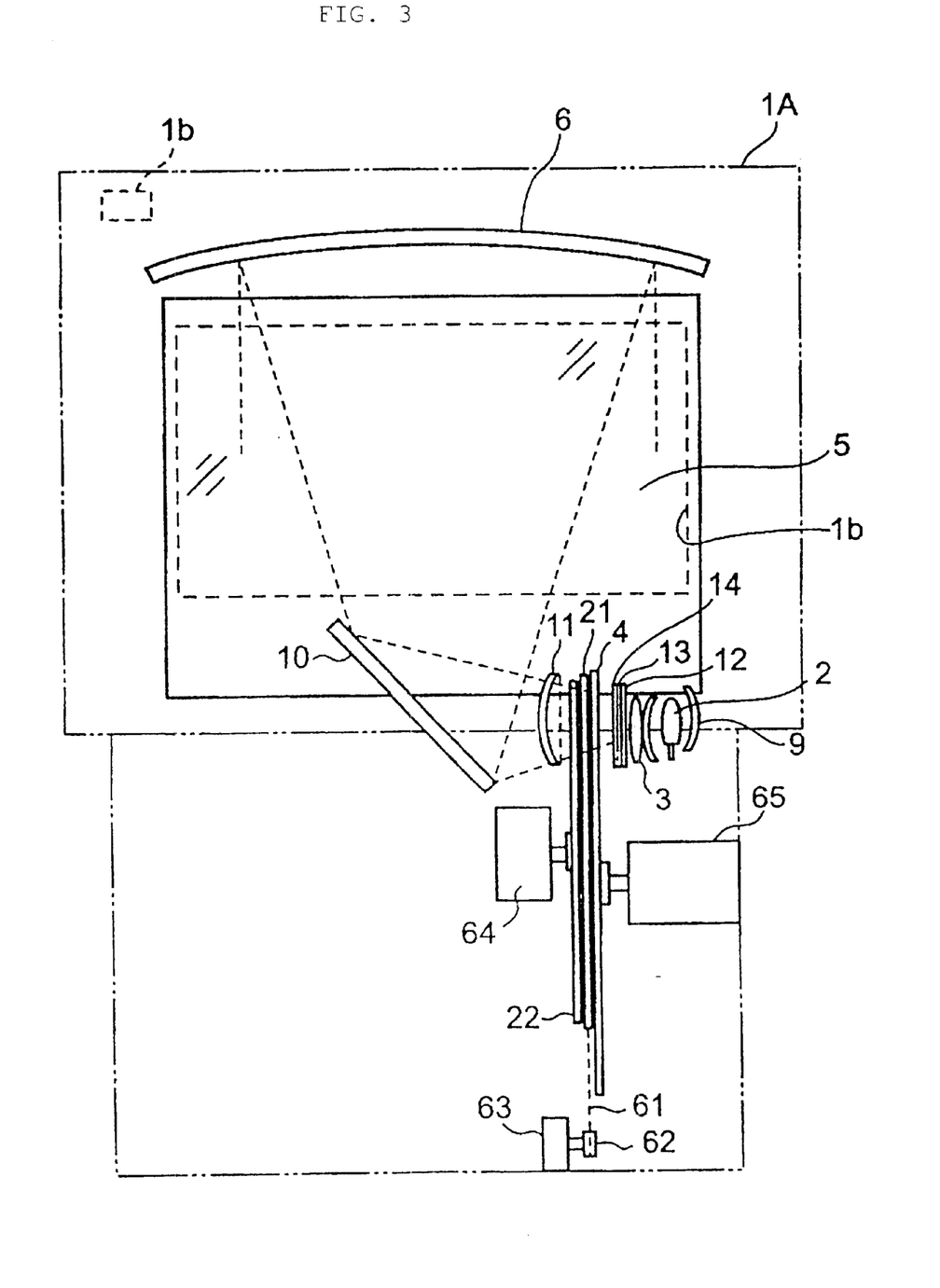
FIG. 3 shows a schematic structure in the case where visual chart displaying means according to the embodiment of the present invention is viewed from the front side thereof.

As shown in FIG. 3, the above box shaped visual chart displaying means 1 includes, inside a case 1A, a light source 2, a reflecting mirror 9, a condenser lens 3, a visual chart plate 4, a diffusing lens 11, a metal mirror 10, a half mirror 5 and a concave mirror 6, and is constructed such that a light flux from the visual chart plate 4 illuminated by the light source 2 through the reflecting mirror 9 and the condenser lens 3 is reflected upward by the metal mirror 10, passed through the half mirror 5, reflected downward by the concave mirror 6, and reflected toward an eye E to be examined by the half mirror 5 which is disposed with the slant of 45° (against both surfaces of the paper in FIG. 3). By changing a slant angle of the half mirror 5 which is disposed with 45°, an alignment to the eye E to be examined in up and down directions is performed.

As a result, when a person to be examined directly views the half mirror 5 in the visual chart displaying means 1, from a rectangular window portion 1b provided in the case 1A of the visual chart displaying means 1, the person may view a visual chart image (virtual image) as an image of a visual chart provided in the visual chart plate 4 with the distance of, for example, 5 m ahead of the eye E to be examined.

A diffusing plate 14 for diffusing and uniformizing a light flux, a filter 13 for removing an infrared light component, and a thermal insulation filter 12 are provided between the condenser lens 3 and the visual chart plate 4.

Further, in the visual chart displaying means 1, as shown in FIG. 3, a mask mechanism is provided between the visual chart plate 4 and the metal mirror 10, which is constructed of, a first disk shaped mask plate 21, a second disk shaped mask plate 22, which are disposed so as to overlap with each other in a minute interval with the visual chart plate 4 and in order, and a mask actuating portion 60 for actuating the first mask plate 21 and the second mask plate 22.

The mask actuating portion 60 is constructed by disposing a first motor 63 and a second motor 64 into the case 1A. The first motor 63 actuates the first mask plate 21 by bridging the circumference of the first mask plate 21 and a drive pulley 62 through a belt 61, and is, for example, a pulse motor. The second motor 64 directly actuates the second mask plate 22 in the center portion thereof, and is, for example, a pulse motor.

Also, the visual chart plate 4 is directly actuated by a visual chart plate motor 65, for example, a pulse motor, which is connected with the center portion of the visual chart plate 4.

Figure 4:
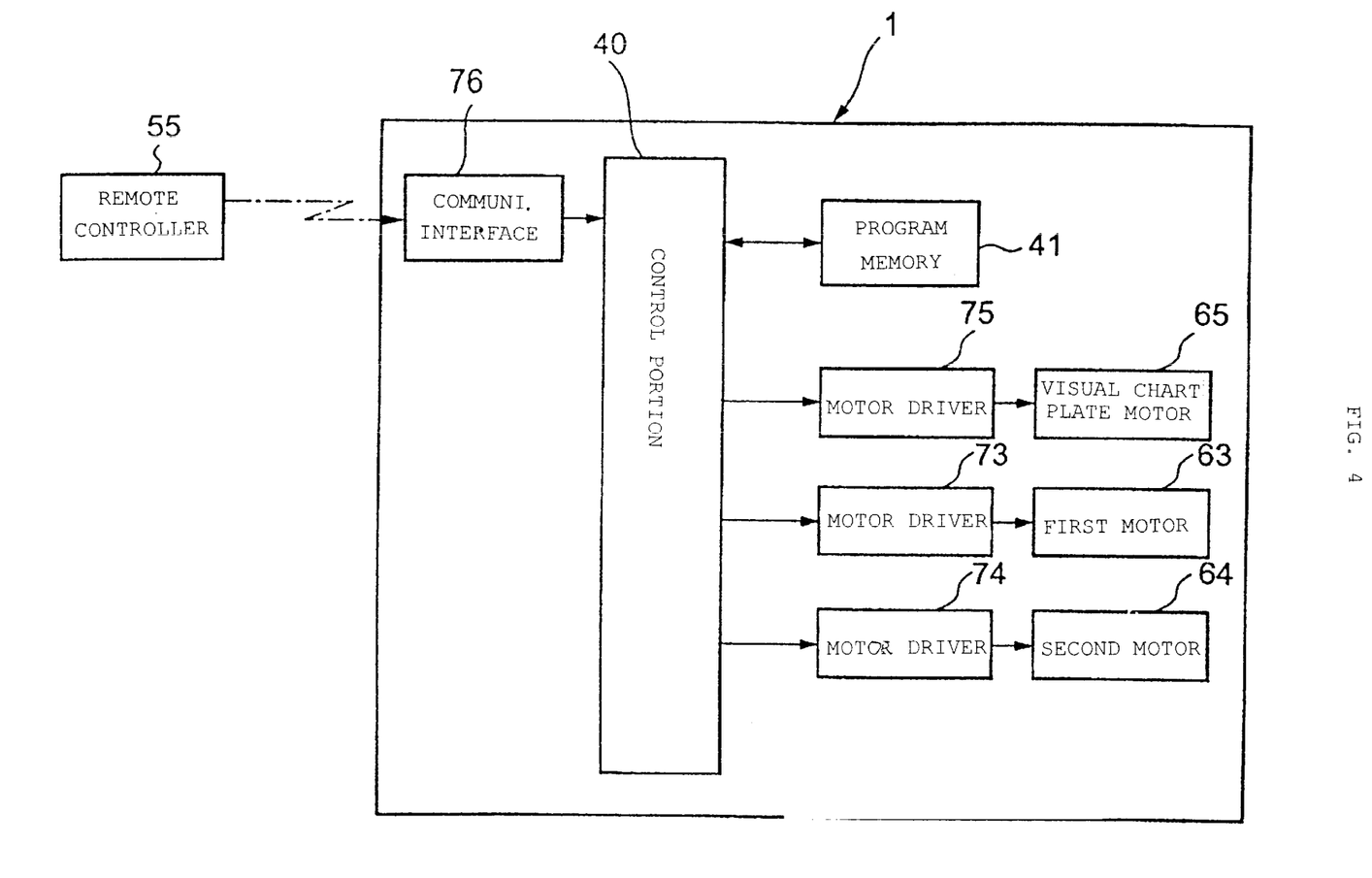
FIG. 4 is a block diagram representing a control system of the visual chart displaying means according to the embodiment of the present invention.

FIG. 4 shows a control system of the visual chart displaying means 1. This control system has a control portion 40 for controlling the entire based on an operation program stored in a program memory 41. Motor drivers 73, 74 and 75 for driving the first motor 63, the second motor 64, the visual chart plate motor 65, respectively, are connected with the control portion 40.

Further, a communication interface 76 for performing communication of various information with the remote controller 55 by wireless is connected with the control portion 40. As shown in FIG. 3, a communication window 1c for the communication interface 76 is provided in, for example, the upper corner portion of the case 1A.

Next, the first mask plate 21 and the second mask plate 22 will be described with reference to FIGS. 5 and 6.

Figure 5:
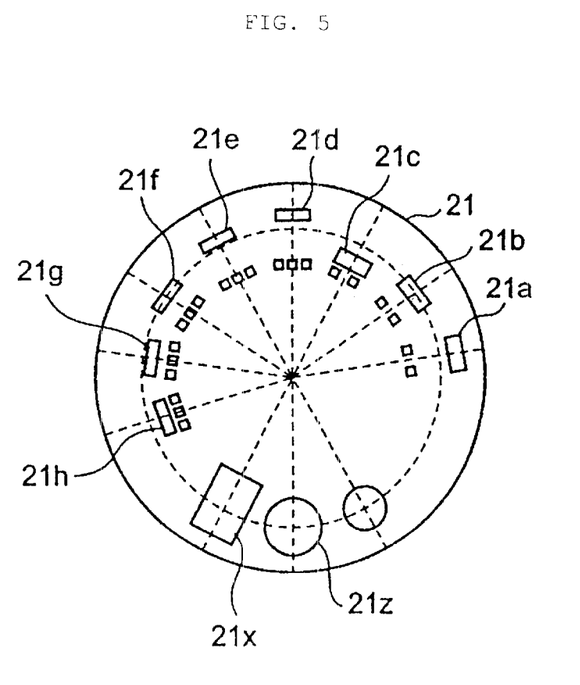
FIG. 5 is a front view of a first mask plate of the visual chart displaying means according to the embodiment of the present invention.

In the first mask plate 21, as shown in FIG. 5, a plurality of non-mask portions 21a to 21h for performing longitudinal direction transmission with respect to each of the visual charts displayed on the visual chart plate 4 are arranged with a circular arrangement. Further, in the first mask plate 21, an opening portion 21x having no mask function, a circular opening portion 21z and the like are arranged with a circular arrangement.

Figure 6:
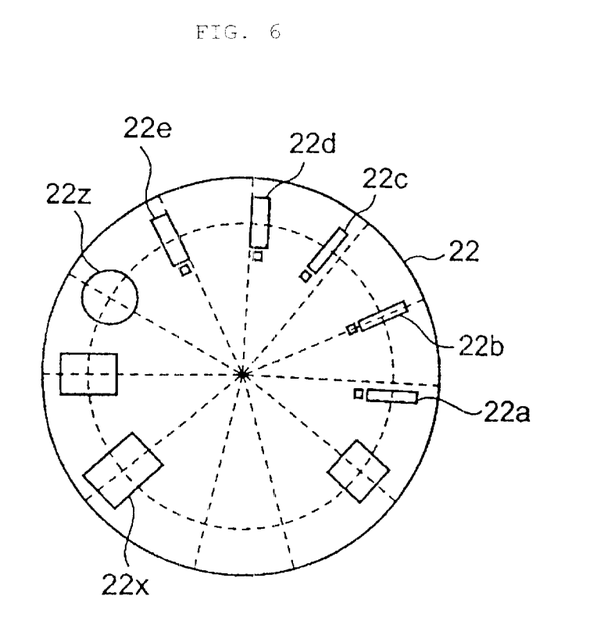
FIG. 6 is a front view of a second mask plate of the visual chart displaying means according to the embodiment of the present invention.

In the second mask plate 22, as shown in FIG. 6, with a state that it is overlapped with the first circular mask plate 21 in the front surface thereof, a plurality of non-mask portions 22a to 22e for performing transverse direction masking with respect to each of the visual charts displayed on the visual chart plate 4 are arranged with a circular arrangement. Further, in the second mask plate 22, an opening portion 22x having no mask function, a circular opening portion 22z and the like are arranged with a circular arrangement.

Figure 7:
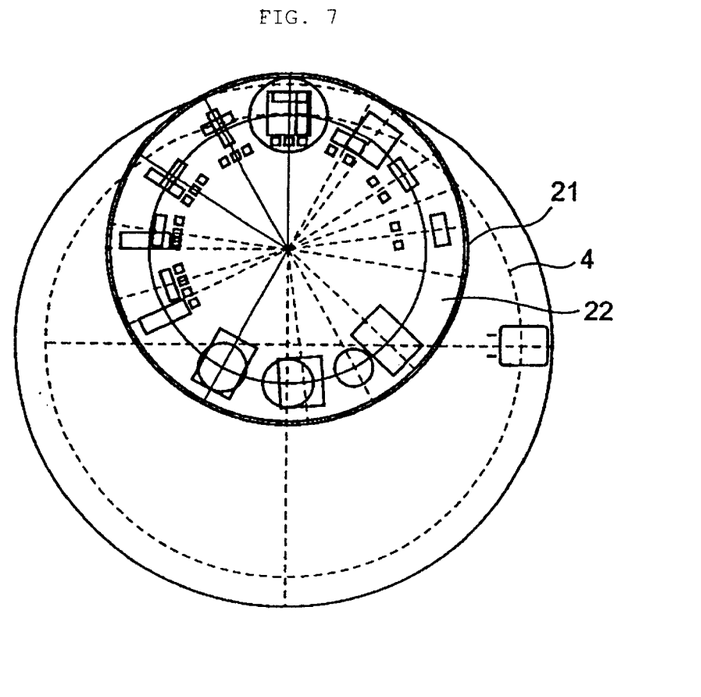
FIG. 7 is a front view representing a state that a visual chart plate, the first mask plate and the second mask plate in the visual chart displaying means according to the embodiment of the present invention are overlapped with each other.

FIG. 7 is a schematic view representing the state that the first mask plate 21 and the second mask plate 22 are overlapped with the visual chart plate 4.

Next, the remote controller 55 will be described with reference to FIG. 8.

Figure 8:
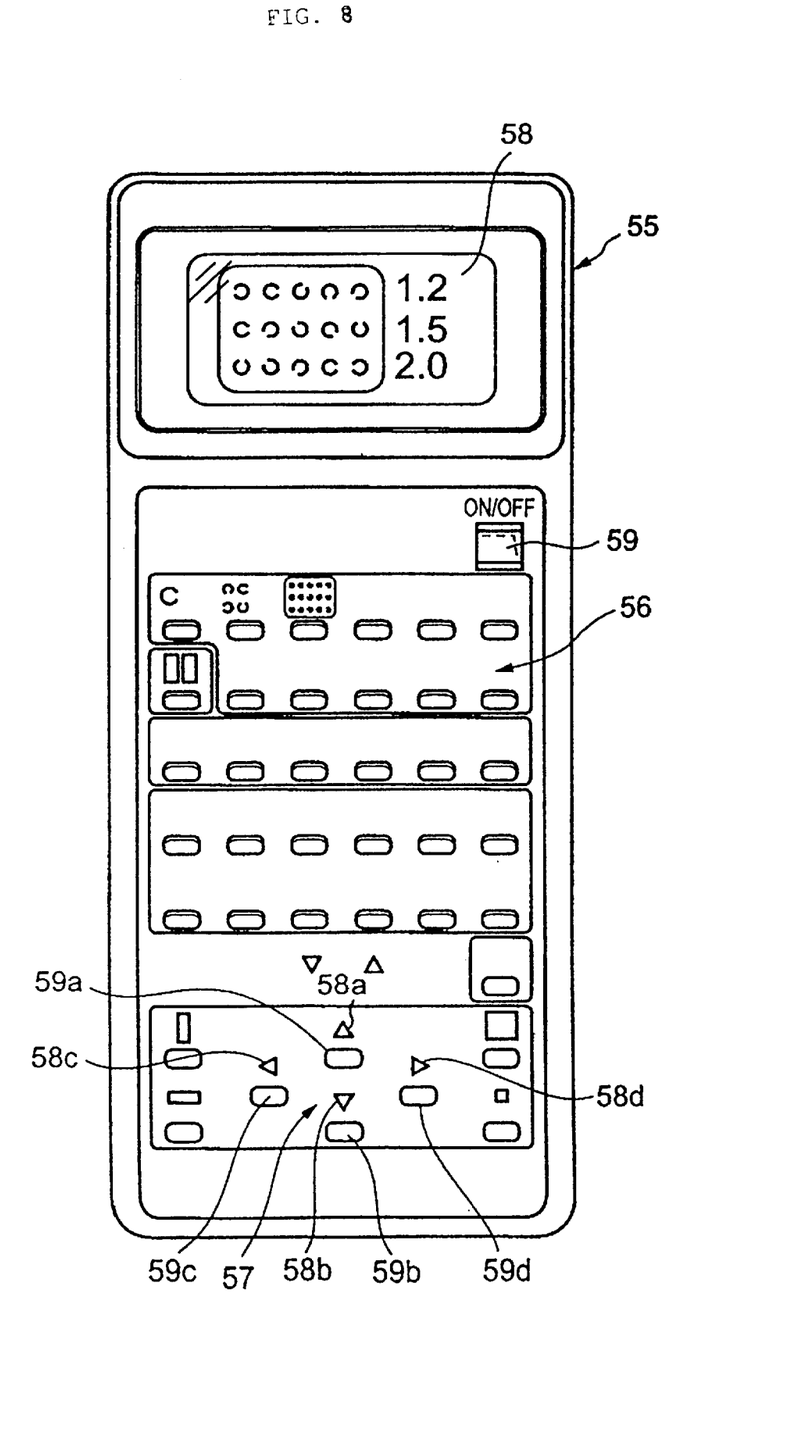
FIG. 8 is a plan view of a remote controller according to the embodiment of the present invention.

As shown in FIG. 8, this remote controller 55 includes, a visual chart operation portion 56 in which visual chart marks corresponding to a large number of visual charts displayed on the visual chart plate 4 are provided and which has respective operation switches, a transmission state instruction portion 57 for instructing a transmission state by using the first mask plate 21 and the second mask plate 22, a display portion 58 for displaying corresponding visual chart marks in response to the operation of the operation switches of the visual chart operation portion 56 (in FIG. 8, Landolt ring marks with respect to 1.2, 1.5 and 2.0, which are arranged with five rows and three columns, are displayed), and a power source switch 59.

In the transmission state instruction portion 57, instruction marks 58a, 58b, 58c and 58d representing up, down, left and right, respectively, an up button 59a, a down button 59b, a left button 59c and a right button 59d are provided.

Next, the operation in the case where a predetermined transmission state with respect to a predetermined visual chart is obtained in the visual chart displaying means 1 according to the embodiment of the present invention will be described with reference to FIG. 9 and the like.

When visual chart marks (which are arranged with five rows and three columns) corresponding to visual acuity values of 1.2, 1.5 and 2.0 are selected by the visual chart operation portion 56 of the remote controller 55, a corresponding signal is transmitted from the remote controller 55 to the control portion 40 through the communication interface 76 by wireless. When this signal is received, the control portion 40 controls the motor driver 75 to drive and rotate the visual chart plate motor 65, so that the visual chart plate 4 is rotated to locate the visual charts (which are arranged with five rows and three columns) corresponding to the visual acuity values of 1.2, 1.5 and 2.0 on an optical path from the light source 2.

Also, with this state, referring to the instruction marks 58a, 58b, 58c and 58d of the transmission state instruction portion 57, the up button 59a, the down button 59b, the left button 59c and the right button 59d are appropriately operated to rotate the first mask plate 21 and the second mask plate 22 as is the case where the visual chart plate 4 is rotated.

Figure 9:
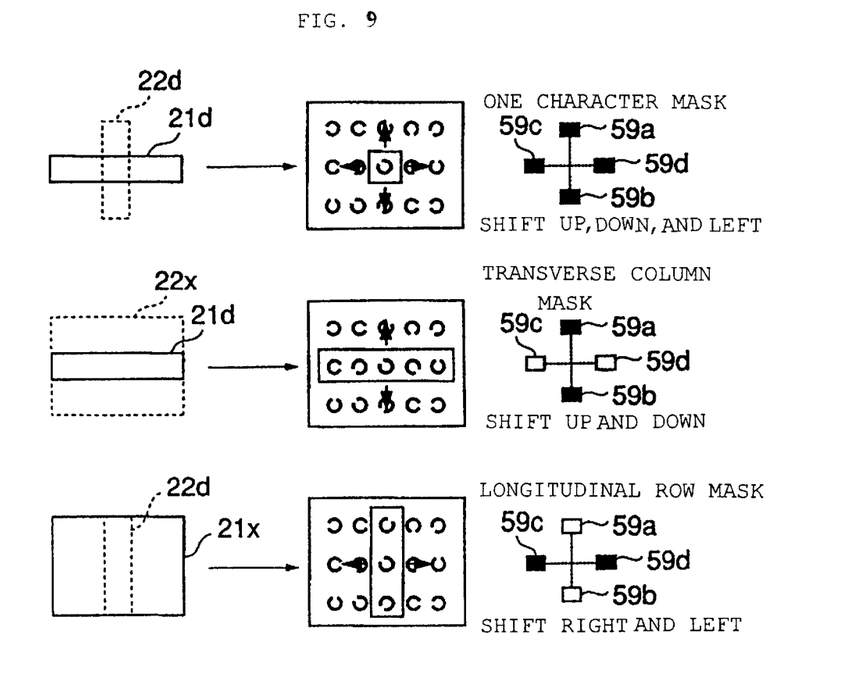
FIG. 9 is an explanatory diagram representing a mask state of the visual chart plate to be masked by the first mask plate or the second mask plate in the visual chart displaying means according to the embodiment of the present invention.

The top in FIG. 9 represents a one character transmission state of the visual charts (which are arranged with five rows and three columns) by the non-mask portion 21d (shown by solid lines) of the first mask plate 21 and the non-mask portion 22d (shown by dotted lines) of the second mask plate 22.

In this case, a one character transmission position can be arbitrary shifted upward, downward, leftward or rightward by operating the up button 59a, the down button 59b, the left button 59c or the right button 59d.

The middle in FIG. 9 represents a single transverse column transmission state of the visual charts (which are arranged with five rows and three columns) by the non-mask portion 21d (shown by solid lines) of the first mask plate 21 and the opening portion 22x (shown by dotted lines) of the second mask plate 22.

In this case, a single transverse column transmission position can be arbitrary shifted upward or downward by operating the up button 59a or the down button 59b.

The bottom in FIG. 9 represents a single longitudinal row transmission state of the visual charts (which are arranged with five rows and three columns) by the opening portion 21x (shown by solid lines) of the first mask plate 21 and the non-mask portion 22d (shown by dotted lines) of the second mask plate 22.

In this case, a single longitudinal row transmission position can be arbitrary shifted leftward or rightward by operating the left button 59c or the right button 59d.

Therefore, according to the embodiment of the present invention, the predetermined visual chart images with a predetermined transmission state can be displayed for the eye E to be examined. Also, since a transmission state by the first mask plate 21 and the second mask plate 22 is changed all at once, the occurrence of the state that the visual chart images viewed by the eye E to be examined appear to flow is prevented. Thus, visual performance examination can be performed without providing the eye E to be examined with uncomfortable feeling.

Further, the visual chart displaying means 1 is constructed by using the first disk shaped mask plate 21 and the second disk shaped mask plate 22. Thus, in comparison with the case where a single circular mask plate is used, the diameter of each of the mask plates can be made small, and thus the visual chart displaying means 1 of a further space saving type can be obtained.

Figure 10:
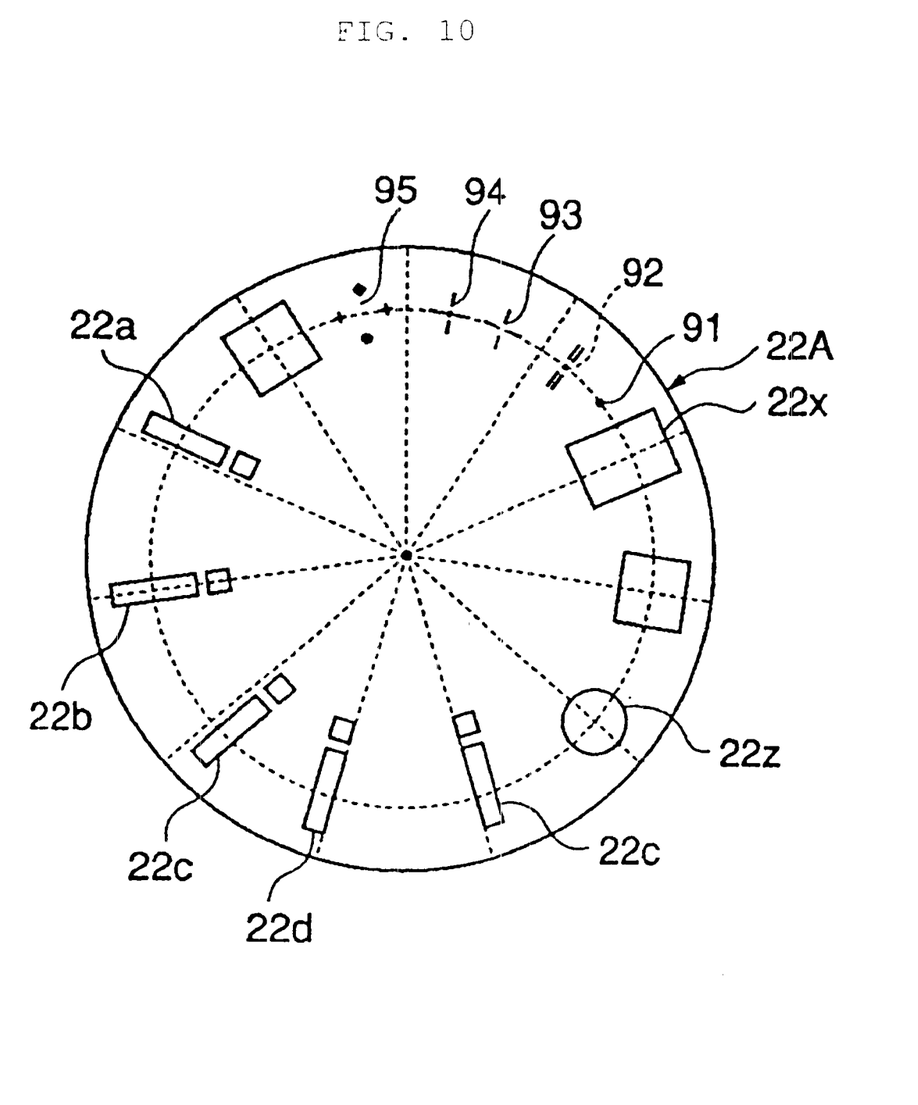
FIG. 10 is a front view representing the case where polarizing visual charts are provided in the second mask plate of the visual chart displaying means according to the embodiment of the present invention.

FIG. 10 shows a modified example of the second mask plate 22. In FIG. 10, a second mask plate 22a is constructed by arranging mainly polarizing visual charts in a circle, in addition to non-mask portions.

Figure 11:
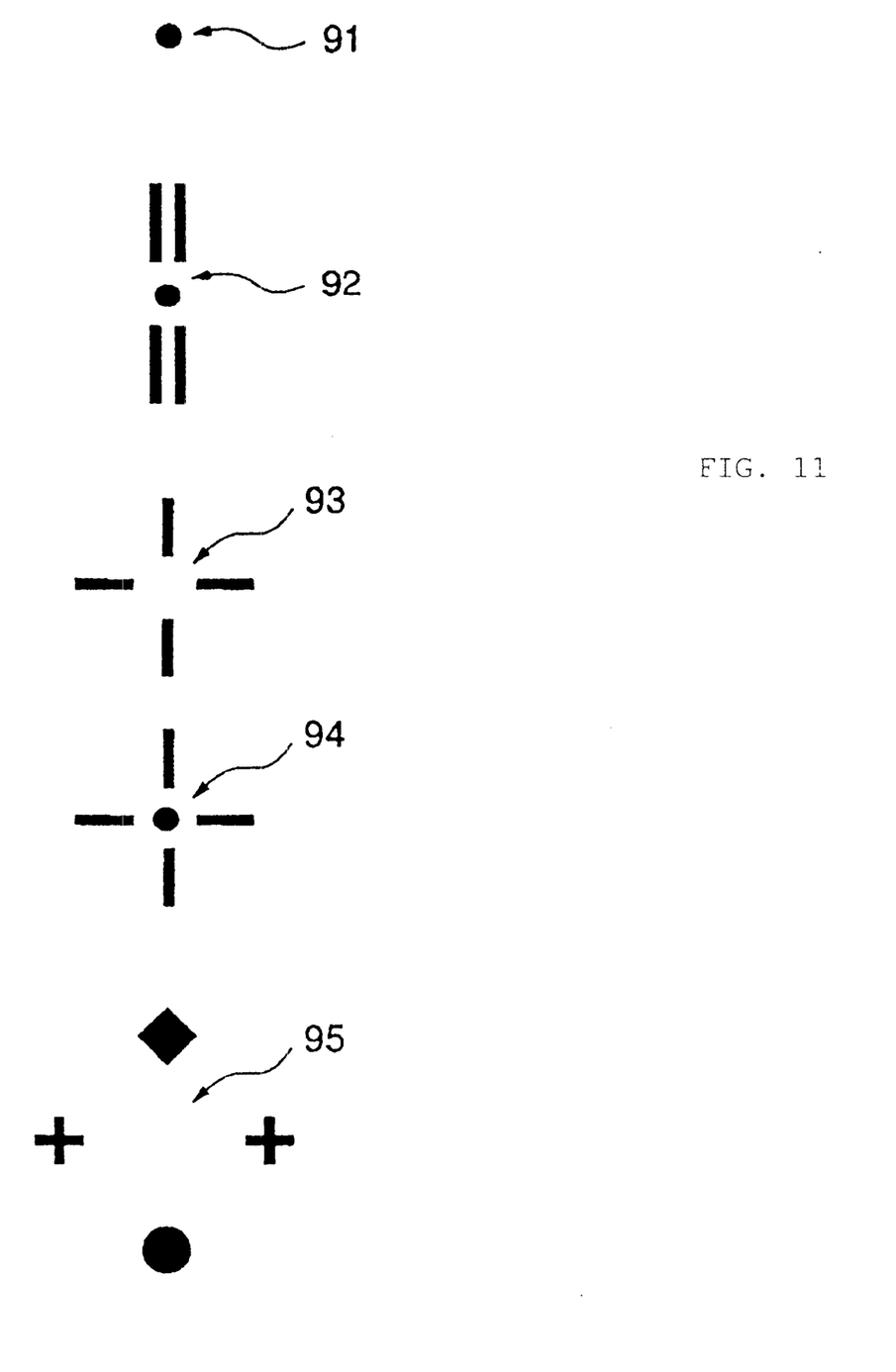
FIG. 11 is an enlarged explanatory diagram representing the polarizing visual charts provided in the second mask plate of the visual chart displaying means according to the embodiment of the present invention.

That is, as shown in FIG. 11 in a magnified form, a fixed point visual chart 91, a Worth's four points visual chart 92, a stereoscopic visual chart 93, a polarizing cross visual chart 94 and a polarizing cross visual chart 95 with a fixed point are arranged in the second mask plate 22a in order.

By using the second mask plate 22a constructed above, the arrangement number of visual charts on the visual chart plate 4 side can be reduced, the diameter of the visual chart plate 4 can be made small, and further the visual chart displaying means 1 can be miniaturized.

Note that a mechanism for non-masking the visual charts by the first mask plate 21 and the second mask plate 22, which are mentioned above, can be also applied to a visual acuity chart displaying apparatus of a panel type for displaying various visual charts, for an eye examination with, for example, the distance of 5 m.

According to the first aspect of the present invention, there can be provided a visual acuity chart displaying apparatus in which a transmission state of a predetermined visual chart can be changed fast and smooth, in which the occurrence of the state that visual chart images viewed by an eye to be examined appear to flow is prevented, and in which a visual performance examination can be performed without providing the eye to be examined with uncomfortable feeling.

According to the second aspect of the present invention, there can be provided a visual acuity chart displaying apparatus in which an effect similar to that of the first aspect is obtained, in which the diameter of a mask plate can be made small, and which can be used as a further space saving type.

Although the visual acuity chart displaying apparatus of the present invention has been described in detail, the present invention is not limited to the above embodiment, and various improvements and modifications may be naturally made in the scope not departing from the gist of the present invention.

What is claimed is:

1. A visual acuity chart displaying apparatus for displaying various visual charts for a visual performance examination, for an eye of a person to be examined, comprising:

a visual chart plate in which a plural kinds of visual charts displayed for the eye to be examined are arranged changeably;

a first mask plate which is disposed in a front of the visual chart plate with an overlapping state and in which a plurality of non-mask portions for performing each single longitudinal row transmission of the visual charts displayed on the visual chart plate are arranged changeably; and a second mask plate which is disposed in a front of the first mask plate with an overlapping state and in which a plurality of non-mask portions for performing each single transverse column transmission of the visual charts displayed on the visual chart plate are arranged changeably, wherein the visual charts with a non-mask state can be displayed for the eye to be examined by a combination of a visual chart changing by the visual chart plate and a non-mask portion changing by the first and second mask plates.

2. A visual acuity chart displaying apparatus for displaying various visual charts for a visual performance examination, for an eye of a person to be examined, comprising:

a visual chart plate in which a plural kinds of visual charts displayed for the eye to be examined are arranged changeably in a circle;

a display optical system for displaying the visual charts of the visual chart plate at a predetermined distance from the eye to be examined;

an illumination optical system including a light source for illuminating the visual charts;

a mask mechanism including, a first mask plate with a disk shape, which is disposed in a front of the visual chart plate with an overlapping state and in which a plurality of first non-mask portions for performing each single longitudinal row transmission of the visual charts displayed on the visual chart plate are arranged changeably, and a second mask plate with a disk shape, which is disposed in a front of the first mask plate with an overlapping state and in which a plurality of second non-mask portions for performing each single transverse column transmission of the visual charts displayed on the visual chart plate are arranged changeably;

indication means for indicating a predetermined transmission state by predetermined visual charts and the plurality of first and second non-mask portions; and a drive system for driving the visual chart plate, the first mask plate and the second mask plate individually to rotate in accordance with indicating information by the indication means, so that visual charts with the predetermined transmission state formed by one selected from the group including a transverse direction, a longitudinal direction and a combination of these directions, are displayed outside a predetermined region of the predetermined visual charts.

3. A visual acuity chart displaying apparatus according to claim 2, wherein the drive system includes a plurality of motors for driving the visual chart plate, the first mask plate and the second mask plate, and control means for controlling the plurality of motors to indicate a predetermined visual chart state.

4. A visual acuity chart displaying apparatus according to claim 3, wherein the control means controls the plurality of motors by remote control.

* * * * *